United States Patent [19]

Iwasawa et al.

[11] Patent Number: 5,864,051

[45] Date of Patent: Jan. 26, 1999

[54] SELECTIVE OXIDATION CATALYST PROCESS FOR PREPARING THE CATALYST AND PROCESS USING THE CATALYST

[75] Inventors: Yasuhiro Iwasawa, Tokyo; Kiyotaka Asakura, Chiba; Tomoya Inoue, Okayama, all of Japan

[73] Assignee: UOP, Des Plaines, Ill.

[21] Appl. No.: 966,738

[22] Filed: Nov. 10, 1997

[51] Int. Cl.⁶ .................................................. C07C 45/34
[52] U.S. Cl. ........................... 568/479; 568/475; 562/537; 502/215
[58] Field of Search ........................ 568/479, 475; 562/534, 537, 538, 542; 502/215, 305, 317, 321

[56] References Cited

U.S. PATENT DOCUMENTS 5,191,116  3/1993  Yamamatsu et al. .................. 562/549
5,276,178  1/1994  Onodera et al. ....................... 562/537
5,329,043  7/1994  Matsuura et al. ...................... 562/534

FOREIGN PATENT DOCUMENTS

05178774-A  7/1993  Japan .

*Primary Examiner*—Shailendra Kumar
*Assistant Examiner*—Sreeni Padmanabhan
*Attorney, Agent, or Firm*—Thomas K. McBride; Frank S. Molinaro

[57] ABSTRACT

A catalyst for the selective oxidation of alkanes and alkenes has been developed. The catalyst consists of a noble metal component such as platinum and a SbOx component. A unique feature of the catalyst is that the noble metal component is present as particles of which from about 1 to about 30 mole % of each particle is in the form of a noble metal/Sb alloy. Optionally a modifier and/or a refractory inorganic oxide may also be added to the catalyst. A process for preparing the catalyst is also presented.

24 Claims, No Drawings

SELECTIVE OXIDATION CATALYST PROCESS FOR PREPARING THE CATALYST AND PROCESS USING THE CATALYST

FIELD OF THE INVENTION

This invention relates to a catalyst for the selective oxidation of alkanes and alkenes, e.g., isobutane to methacrolein and isobutylene to methacrolein, a process for preparing the catalyst and a process using the catalyst. The catalyst consists of a noble metal component, e.g., platinum, a SbOx component and optionally a modifier. At least a fraction of the noble metal is alloyed with the SbOx component.

BACKGROUND OF THE INVENTION

The selective oxidation of various hydrocarbons to oxygen containing compounds (aldehydes, ketones) has received considerable attention since the oxygen containing compounds have many commercial applications. Usually the reaction involves the selective oxidation of olefins to aldehydes or ketones. However, it would be more beneficial to convert alkanes to aldehydes and ketones.

The art discloses some catalysts which are stated to be useful for the selective oxidation of alkanes. For example the use of scheelite type oxides has been reported in *Appl. Catal.* 70, 189 (1991). The use of V—Sb—O has been reported in *Appl. Catal.* 33, 343 (1987). The use of di-vanadyl pyrophosphate to produce methacrolein from isobutane has been reported in U.S. Pat. No. 5,329,043. The use of gold and/or silver containing vanadium pyrophosphate catalysts is reported in JPO5178774-A. Finally, U.S. Pat. No. 5,191,116 discloses a molybdenum hetero-polyacid catalyst.

In contrast to this art, applicants have developed a simple catalyst which is very active in the conversion of both alkanes and alkenes to oxygen containing organic compounds. This catalyst contains a noble metal such as platinum and an SbOx component where x varies from about 1.5 to about 2.5. The catalyst is characterized in that the noble metal particles and the SbOx component form an alloy. Finally, the catalyst can also contain a promoter and/or a refractory inorganic oxide.

SUMMARY OF THE INVENTION

As stated, this invention relates to a catalyst composition for the selective oxidation of alkanes and alkenes, a process for preparing the catalyst and a process using the catalyst. Accordingly, one embodiment of the invention is a catalyst composition for the selective oxidation of hydrocarbons comprising a noble metal component, and a SbOx component, where x varies from about 1.5 to about 2.5, the catalyst characterized in that the noble metal is present as particles of which from about 1 mole % to about 30 mole % of each particle is in the form of a noble metal/Sb alloy.

Another embodiment of the invention is a process for preparing a catalyst composition comprising a noble metal component, and a SbOx component, where x varies from about 1.5 to about 2.5, the catalyst characterized in that the noble metal is present as particles of which from about 1 mole % to about 30 mole % of each particle is in the form of noble metal/Sb alloy, the process comprising impregnating the SbOx component with a solution of a noble metal compound and calcining the impregnated SbOx at a temperature of about 400° C. to about 600° C. at a time sufficient to provide the composition.

Yet another embodiment of the invention is a process for the selective oxidation of hydrocarbons comprising contacting a feed stream containing at least one hydrocarbon and oxygen with a selective oxidation catalyst at selective oxidation conditions to provide an oxidized hydrocarbon, the catalyst comprising a noble metal component, and a SbOx component, where x varies from about 1.5 to about 2.5, the catalyst characterized in that the noble metal is present as particles of which from about 1 mole % to about 30 mole % of each particle is in the form of a noble metal/Sb alloy.

These and other objects and embodiments will become more clear after a detailed description of the invention.

DETAILED DESCRIPTION OF THE INVENTION

One embodiment of the present invention is a catalyst for the selective oxidation of hydrocarbons. The catalyst comprises a noble metal component, a SbOx component, optionally a promoter and/or a refractory inorganic oxide. Accordingly, one necessary component of the present catalyst composition is antimony suboxide, SbOx where x has a value of about 1.5 to about 2.5. Without wishing to be bound by any particular theory, it appears that one of the active forms of the SbOx component has the empirical formula $Sb_6O_{13}$.

The source of the SbOx component is not important. Therefore, antimony oxide can be obtained commercially, e.g., $Sb_2O_5$ or the SbOx component can be prepared by the hydrolysis of antimony compounds such as $SbCl_5$. The resulting oxide is dried and then calcined at a temperature of about 300° C. to about 500° C.

On the SbOx component is now deposited a noble metal component. The noble metal is selected from the group consisting of platinum, palladium, rhodium, ruthenium, iridium and mixtures thereof. The noble metals are deposited onto the SbOx component by conventional means such as impregnation, spray drying, etc., using a solution of a noble metal compound. The noble metal compounds which can be used include salts such as the halides, nitrates, acetates and sulfates. Specific examples include chloroplatinic acid ($H_2PtCl_6$), platinum chloride, platinum nitrate, palladic acid, palladium chloride, palladium nitrate, palladium acetate, rhodium chloride, rhodium nitrate, ruthenium chloride, ruthenium nitrate, iridium sulfate, iridium chloride and iridium bromide.

Other noble metal compounds which can be used include noble metal amine compounds and organo compounds such as palladium acetylacetonate ($Pd(acac)_2$), rhodium acetylacetonate ($Rh(acac)_3$), platinum acetylacetonate ($Pt(acac)_2$), platinum acetate complex ($Pt_4(C_2H_3O_2)_8$, acetylacetonato (ethylene)rhodium (I), hexarhodium hexadecacarbonyl, bis (cyclopentadienyl)ruthenium, ruthenium (III) acetylacetonate, ruthenium carbonyl, chloro-1,5-cyclooctadiene iridium (I) dimer, dicarbonylacetylacetonato iridium (I) and [$Pt(NH_3)_6Cl_2$], hexaamine platinum (IV) chloride.

A solution of the desired noble metal compound is prepared by dissolving the desired compound either in water or an organic solvent. For example most of the noble metal salts are soluble in water, while some of the organo-metallic compounds are only soluble in organic solvents. For example $Pt(acac)_2$ is soluble in acetone and thus it is most convenient to prepare an acetone solution of $Pt(acac)_2$.

Having formed the desired noble metal solution, it is used to deposit the noble metal onto the SbOx component by conventional methods such as impregnation, spray drying, etc. Usually, the SbOx component is contacted with the noble metal solution, the resulting mixture is then dried and calcined at a temperature of about 400° C. to about 600° C. for a time of about 1 hour to about 24 hours. The amount of noble metal which is dispersed on the SbOx component can vary widely, but generally is from about 0.01 to about 10 wt. % and preferably from about 0.1 to about 5 wt. % with respect to the total catalyst weight.

Next, it is necessary to carry out a partial reduction step which involves treating the calcined catalyst with a mixture of a hydrocarbon and oxygen at a temperature of about 200° C. to about 500° C. for a time of about 1 hour to about 24 hours. This activation step can be a separate step or it can be performed in situ prior to carrying out the selective oxidation process described herein. The hydrocarbon which is used is an alkane or alkene having from 2 to 15 carbon atoms and the molar ratios of hydrocarbon to oxygen can vary from about 10:1 to about 1:5. If a separate reduction step is carried out, hydrogen or other reductants well known in the art can be used.

A particular characteristic of the present catalyst of the invention is that the noble metals exist as particles on the SbOx component and more importantly, these particles form an alloy with the SbOx component, i.e., noble metal/Sb alloy. It has been found that only a portion of each noble metal particle is alloyed with the Sb, which portion varies from about 1% to about 30%. Usually noble metal/Sb, e.g., Pt—Sb, alloy formation occurs at the surface of the particle, but can extend to the interior of the particle.

The catalyst described above can also contain one or more promoter or modifier selected from the group consisting of Ti, V, Nb, Mo, Fe, Co, In, Ge, Sn, Bi, Te, Group IA, Group IIA, and Group IIIB metals. These modifiers can be added to the SbOx by co-precipitation or impregnation. Thus modifier compounds such as halide, nitrate, etc. salts or complexes such as organic chelate complexes can be used to prepare a solution which is then used to co-precipitate with an antimony component solution or to impregnate the SbOx component, followed by drying and calcination. If the modifier is impregnated onto the SbOx, this can be done before, after or simultaneously with the noble metal component though not necessarily with equivalent results. The amount of modifier can vary considerably, but is usually an amount from about 0.1 to about 30 wt. % with respect to the total catalyst weight.

Yet another optional component of the catalyst of the invention is a refractory inorganic oxide selected from the group consisting of silica, zirconia, alumina, clay, zeolites and mixtures thereof. Included among the zeolites which can be used are: X, Y, β, ω, MFI, ALPO, and SAPO. The refractory oxide can be incorporated as a binder or support.

The catalysts described above are useful in various hydrocarbon conversion processes. One such process is the selective oxidation of hydrocarbons. The hydrocarbons to be used in this process are alkanes and alkenes. By selective oxidation is meant the oxidation of the hydrocarbon to the corresponding aldehyde. An example of this selective oxidation is the conversion of isobutane or isobutylene to methacrolein (MAL) or 2-methyl-propenal. It is to be understood that alkanes and alkenes other than isobutane or isobutylene can be used in this selective oxidation process. Generally, alkanes and alkenes with carbon numbers from 2 to 15 can be used. This includes linear, branched and cyclic alkanes and alkenes. Specific examples of the alkanes which can be used in the present process include ethane, propane, n-butane, isobutane, n-pentane, isopentane, 2-methyl heptane, n-nonane, cyclohexane, methyl cyclohexane, n-dodecane, and 2,2,-dimethyl dodecane. Specific examples of the alkenes which can be used in the present process include ethene, propene, butene-1, isobutylene, pentene-2, 2-methyl butene-2, 2-methyl heptene-1, octene-1, cyclohexene, dodecene-1, and 2-methyl dodecene-2.

The process is carried out by placing the catalyst in a reactor and contacting the feed stream which contains the desired hydrocarbons with the catalyst in the presence of oxygen. The type of reactor which can be used is any type well known in the art such as fixed-bed, moving-bed, fluidized bed, etc. The feed stream can be flowed over the catalyst bed either up-flow or down-flow. In the case of a fluidized-bed, the feed stream can be flowed cocurrent or counter-current.

The feed stream used in the present process will contain the desired alkane along with oxygen. Oxygen can be introduced either as pure oxygen or as air. The molar ratio of oxygen ($O_2$) to alkane can range from about 5:1 to about 1:10. In addition to oxygen and alkane, the feed stream can also contain a diluent gas selected form nitrogen, neon, argon, helium, carbon dioxide, steam or mixtures thereof. As stated the oxygen can be added as air which could also provide a diluent. The molar ratio of diluent gas to oxygen ranges from greater than zero to about 10:1.

The catalyst and feed stream are reacted at selective oxidation conditions which include a temperature of about 300° C. to about 600° C., a pressure of about 101 kPa to about 5,066 kPa and a space velocity of about 100 to about 100,000 $hr^{-1}$.

The following examples are presented in illustration of the invention and are not intended as undue limitations on the generally broad scope of the invention as set out in the appended claims.

Example 1

In a container, 25 g of $SbCl_5$ was slowly added to 100 g of water and heated over a water bath. To this mixture, concentrated hydrochloric acid was added until the $SbCl_5$ completely dissolved. Next 100 g of an ammonium hydroxide solution (10%$NH_4OH$) was added to hydrolyze the $SbCl_5$. The precipitated solid was filtered, dried at 125° C. for 2 hours and calcined at 500° C. for 2 hours to give SbOx.

Platinum was deposited on the SbOx prepared above by taking 3 g of SbOx and impregnating it with 2 ml of a solution of 0.03 g of platinum acetylacetonate dissolved in acetone. The impregnated powder was dried at 50° C. and then calcined at 500° C. for 2 hours. Analysis of this catalyst showed it contained 0.5 wt. % platinum. This catalyst was identified as catalyst A.

Example 2

The procedure of example 1 was used to prepared a Pt/SbOx catalyst with 2.0 wt. % platinum. This catalyst was identified as catalyst B.

Example 3

Catalyst A and catalyst B were analyzed by EXAFS to determine the type of bonds and coordination number of those bonds. Analyses were conducted after: calcination at 500° C.; oxidation of iso-butane; oxidation of iso-butylene and reduction with hydrogen at 200° C. The results of these analyses are presented in Table 1.

TABLE 1

EXAFS Analysis of Pt—SbOx Catalysts

| Catalyst I.D. | Bond | Coordination No. |
|---|---|---|
| Cat. A (calcined) | Pt—Pt | 10.3 |
| Cat. B (calcined) | Pt—Pt | 11.8 |
| Cat. A (i-C$_4$H$_{10}$ox.) | Pt—Pt | 11.7 |
| Cat. B (i-C$_4$H$_{10}$ox.) | Pt—Pt | 10.8 |
| Cat. A (i-C$_4$H$_8$ox.) | Pt—Pt | 10.9 |
| Cat. B (i-C$_4$H$_8$ox.) | Pt—Pt | 11.5 |
| Cat. B (H$_2$red.) | Pt—Pt | 6.1 |
| Cat. B (H$_2$red.) | Pt—Sb | 0.6 |
| Pt foil | Pt—Pt | 12.0 |

The data in Table 1 indicate that for the calcined catalysts neither isolated Pt ions nor Pt oxide is present. Comparison to the Pt-foil indicates that metallic bulk platinum particles are present. Very little change is observed after oxidation of either iso-butane or iso-butylene. However, after reduction with hydrogen, the presence of Pt—Sb bonds are observed along with a decrease in Pt—Pt coordination number. This is evidence that Pt—Sb alloy formation has occurred.

Catalysts A and B were also analyzed by hydrogen chemisorption. Analyses were conducted after: calcination at 500° C.; oxidation of iso-butane at 500° C. and reduction with hydrogen at 200° C. The results of these analyses are presented in Table 2.

TABLE 2

Hydrogen Chemisorption (H/PT) for Pt—SbOx Catalysts

| Catalyst I.D. | Condition | H/Pt |
|---|---|---|
| Catalyst A | Calcined | 0.07 |
| Catalyst B | Calcined | 0.24 |
| Catalyst A | H$_2$ Reduced | 0.0 |
| Catalyst B | H$_2$ Reduced | 0.0 |
| Catalyst B | i-C$_4$H$_{10}$Ox | 0.01 |
| Catalyst B | i-C$_4$H$_8$Ox | 0.01 |

The results in Table 2 show a dramatic decrease in hydrogen adsorption after both hydrogen reduction and both of the oxidation reactions. However, both XRD and EXAFS do not show a significant change in particle size. Therefore, this shows that a Pt—Sb alloy is present on the surface of the platinum particles.

Example 4

Catalyst A was tested for the oxidation of iso-butane as follows. A 0.3 g sample was placed in a quartz tube which was heated at 500° C. for 2 hours in an O$_2$/He(20%) gas mixture and then cooled to room temperature. Next a gas mixture of 20% isobutane, 4% oxygen and the remainder helium was flowed through the catalyst at a rate of 2,400 mL/hr and the temperature raised to 500° C. and held there for 2 hours at which time the steady state selective oxidation of iso-butane to methacrolein (MAL) was measured. Catalyst A produced 0.98% MAL.

Example 5

Catalyst A was tested for the selective oxidation of iso-butylene in the same way as in example 4 except that the test gas contained 1.7% isobutylene instead of the isobutane. The MAL yield was found to be 23%.

We claim as our invention:

1. A catalyst composition for the selective oxidation of hydrocarbon comprising a noble metal component, and a SbOx component, where x varies from about 1.5 to about 2.5, the catalyst characterized in that the noble metal is present as particles of which from about 1 mole % to about 30 mole % of each particle is in the form of a noble metal/Sb alloy.

2. The composition of claim 1 where the noble metal is selected from the group consisting of platinum, palladium, rhodium, ruthenium, iridium and mixtures thereof.

3. The composition of claim 2 where the noble metal is platinum.

4. The composition of claim 1 where the noble metal is present in an amount from about to 0.1 to about 5 wt. %.

5. The composition of claim 1 further characterized in that it contains a modifier selected from the group consisting of Ti, V, Nb, Mo, Fe, Co, In, Ge, Sn, Bi, Te, Group IA, Group IIA, and Group IIIB elements.

6. The composition of claim 1 further characterized in that it contains a refractory inorganic oxide selected from the group consisting of silica, zirconia, alumina, clay, zeolites and mixtures thereof.

7. A process for preparing a catalyst composition comprising a noble metal component, and a SbOx component, where x varies from about 1.5 to about 2.5, the catalyst characterized in that the noble metal is present as particles of which from about 1 mole % to about 30 mole % of each particle is in the form of a noble metal/Sb alloy, the process comprising impregnating the SbOx component with a solution of a noble metal compound, calcining the impregnated SbOx at a temperature of about 400° C. to about 600° C. for a time sufficient to calcine the composition and reducing the calcined catalyst with a mixture of a hydrocarbon and oxygen at a temperature of about 200° C. to about 500° C. for a time of about 1 to about 2 hours thereby providing said catalyst composition.

8. The process of claim 7 where the noble metal is selected from the group consisting of platinum, palladium, rhodium, ruthenium, iridium and mixtures thereof.

9. The process of claim 8 where the noble metal is platinum.

10. The process of claim 7 where the noble metal is present in an amount from about 0.1 to about 5 wt. %.

11. The process of claim 7 where the noble metal compound is selected from the group consisting of noble metal organo compounds, halide salts, nitrate salts, acetate salts, sulfate salts, and amine compounds.

12. The process of claim 11 where the noble metal organo compound is platinum acetylacetonate.

13. The process of claim 7 where the calcination time varies from about 1 hour to about 24 hours.

14. The process of claim 7 where the hydrocarbon is an alkane or alkene having from 2 to 15 carbon atoms and the molar ratio of hydrocarbon to oxygen varies from about 10:1 to about 1:5.

15. The process of claim 7 further characterized in that the composition contains a modifier selected from the group consisting of Ti, V, Nb, Mo, Fe, Co, In, Ge, Sn, Bi, Te, Group IA, Group IIA and Group IIIB elements, and the modifier is deposited on the composition by impregnating the calcined composition with a solution of a modifier compound and calcining the modifier impregnated composition.

16. The process of claim 15 where the modifier compound is selected from the group consisting of the halide or nitrate salts.

17. A process for the selective oxidation of alkanes comprising contacting a feed stream containing at least one alkane and oxygen with a selective oxidation catalyst at selective oxidation conditions to provide an oxidized alkane, the catalyst comprising a noble metal component, and a SbOx component, where x varies from about 1.5 to about 2.5, the catalyst characterized in that the noble metal is present as particles of which from about 1 mole % to about 30 mole % of each particle is in the form of a noble metal/Sb alloy.

18. The process of claim 17 where the alkane has from 2 to 15 carbon atoms.

19. The process of claim 17 where the molar ratio of oxygen to alkane varies from about 5:1 to about 1:10.

20. The process of claim 17 where the selective oxidation conditions include a temperature of about 300° C. to about 600° C., a pressure of about 101 kPa to about 5,066 kPa and a space velocity of about 100 to about 100,000 $hr^{-1}$.

21. The process of claim 17 further characterized in that the feed mixture also contains a diluent gas selected from the group consisting of nitrogen, neon, argon, helium, carbon dioxide and steam.

22. The process of claim 21 where the molar ratio of diluent gas to oxygen ranges from greater than zero up to about 10:1.

23. The process of claim 17 where the noble metal is selected from the group consisting of platinum, palladium, rhodium, iridium and mixtures thereof.

24. The process of claim 23 where the noble metal is platinum.

* * * * *